United States Patent [19]

Engel et al.

[11] Patent Number: 5,110,814
[45] Date of Patent: May 5, 1992

[54] AZELASTINE AND ITS SALTS USED TO COMBAT PSORIASIS

[75] Inventors: Jürgen Engel, Alzenau, Fed. Rep. of Germany; Michael Molliere, Rutherford, N.J.; Istvan Szelenyi, Schwaig, Fed. Rep. of Germany

[73] Assignee: Asta Pharma AG, Fed. Rep. of Germany

[21] Appl. No.: 458,350

[22] Filed: Dec. 28, 1989

[30] Foreign Application Priority Data

Jan. 11, 1989 [DE] Fed. Rep. of Germany ....... 3900607

[51] Int. Cl.$^5$ .............................................. A61K 31/55
[52] U.S. Cl. .................................... 514/212; 514/863
[58] Field of Search ................................. 514/212, 863

[56] References Cited

U.S. PATENT DOCUMENTS 4,871,733 10/1989 Sunshine et al. ................... 514/212

OTHER PUBLICATIONS

M. Kondo, Jpn. J. Clin. Ophthalmol. 42, (1988), p. 781.
N. Chand, Br. J. Pharmacol. 87 (2), (1986), p. 443.
N. Chand, Allergy, 41, (1986), p. 473.
K. Taniguchi, Biochem. Pharmacol., 33 (20), (1984), p. 3165.
J. G. Massicot, Prostaglandins, 32 (4), (1986), p. 481.
Arzneim.-Forsch/Drug Res., 31 (2), 8, (1981), pp. 1212–1215, 1184–1193, 1193–1195, 1196–1203 and 1203–1206.
Arerugi, 1987, 36 (2), pp. 108–111 (CA-107:33156m).
Agents Actions, 1989, 26 (1-2), pp. 70–72 (CA-110:88346r).
Gastroenterol. Jpn., 1988, 23 (3), pp. 263–267 (CA-109:108425a).
J. Pharm. Pharmacol., 1988, 40 (3), p. 225 (CA-108:197821w).
Eur. J. Pharmacol., 1988, 148 (1), pp. 35–41 (CA-108:179821s).
Int. Arch. Allergy Appl. Immunol., 1987, 83 (3), pp. 284–290 (CA-107:70437z).
Chemical Abstracts 95:180848a (1981).

Primary Examiner—Leonard Schenkman
Attorney, Agent, or Firm—Cushman, Darby & Cushman

[57] ABSTRACT

The use of azelastine or its therapeutically acceptable salts and the preparation of a pharmaceutical composition for the treatment of inflammatory disorders and psoriasis disorders.

6 Claims, No Drawings

AZELASTINE AND ITS SALTS USED TO COMBAT PSORIASIS

The present invention relates of azelastine as an anti-inflammatory agent in the treatment of psoriasis and related disorders.

BACKGROUND OF THE INVENTION

The pharmaceutically active substance azelastine (chemical designation 4-(p-chloro-benyzl)-2-(hexahydro-1-methyl-1H-azepine-4-yl)-1-(2H)-phthalazinone) is known to be useful in asthma prophylaxis and as an anti-allergic agent (see German Patent 21 64 058).

SUMMARY OF THE INVENTION

In accordance with the present invention, it has been found that azelastine has anti-inflammatory effects which are useful in the treatment of psoriasis and disorders related thereto. The term psoriasis disorders is understood in the context of the invention as relating to skin disorders which are accompanied by hyperkeratoses, such as in particular psoriasis. The present invention also relates to the treatment of other inflammatory disorders, for example, the treatment of *Colitis ulcerosa*.

THE EFFECT OF AZELASTINE IN PSORIASIS DISORDERS AND DISORDERS RELATED THERETO (FOR EXAMPLE PSORIASIS) AND THE TESTING OF THIS EFFECT.

In order to evaluate the effects of azelastine in accordance with the present invention, mice (average weight 25 g) were given 1 mg/kg of azelastine daily for 7 days. On day 8, the top layer of skin was removed using sandpaper. This mechanical irritation and removal of the upper layer of skin causes an acute reaction which has morphological similarities with the psoriatic reaction. In addition, the leukotriene content of the dermis and epidermis increases. This is accompanied by a fall in prostaglandin concentration. These changes, too, are typical for psoriasis. These changes did not occur if the mice had been treated with azelastine. Azelastine normalizes or even lowers dermal and/or epidermal leukotriene concentration and increases prostaglandin concentration.

Currently, psoriasis is principally treated using corticosteroids. In comparison to that treatment, azelastine has only slight or negligible side effects and also inhibits leukotriene synthesis in the skin after systemic administration; in addition azelastine also inhibits the formation of edema induced by PAF (platelet activating factor).

Pharmaceutical formulations for application in psoriasis disorders and disorders related thereto in humans generally contain between 2 to 16, preferably 4 to 8 mg of azelastine. Suitable forms of azelastine for administration may include, for example, tablets, capsules, pills, coated tablets, suppositories, ointments, gels, creams, powders, dusting powders, aerosols and liquids. Liquid forms of application that may, for example, be considered are: oils or alcoholic or aqueous solutions as well as suspensions and emulsions. Preferred forms of application are tablets which contain between 4 and 8 mg or solutions which contain between 0.1 to 10 percent by weight of azelastine.

The single dose of azelastine for application in psoriasis disorders and disorders related thereto may for example lie:

a) in oral medicinal forms, between 2 and 16 mg, preferably 8 mg:
b) in medicinal forms for local application on the skin and mucous membranes (for example in the form of solutions, lotions, emulsions. ointments and the like), between 0.1 and 10% by weight, preferably 0.7-5% by weight, in particular 1-5% by weight.

One to 2 tablets, 3 times daily, containing 4 to 8 mg of azelastine may for example be recommended. In the case of oral administration the minimum daily dose is for example 4 mg; the maximum daily dose in oral administration should not exceed 24 mg. - (The doses are in each case related to the free base) -

THE EFFECT OF AZELASTINE IN INFLAMMATORY DISORDERS AND THE TESTING OF THIS EFFECT

After local application, azelastine inhibits the development of edema of the ear of the mouse to a dose-related extent after local application of 12-0-tetradecanoylphorbol-acetate (TPA) or arachidonic acid. (Method of Young et al.).

In addition azelastine displays quite generally a good anti-inflammatory effect both after topical (local) and after systemic administration. This effect was for example tested on carrageenin-induced paw edema of the rat (Method after Mörsdorf et al., Arch. Int. Pharmacodyn. 192 (1971) page 111) or on chemically-induced mouse ear edema (Method of Young et al., Journal of Investigative Dermatology 80 (1983) page 48–52 as well as 82 (1984) page 367).

In the experimental model of carrageenin-induced paw edema of the rat after oral administration (Mörsdorf et al. 1971) the test substances are administered orally two hours before administration of the carrageenin using an esophageal tube (intragastrally). The extent of the increase of paw volume is measured one hour later. Using this process (reduction of the exposure time from the conventional three hours to one hour), the effect of the test substances on the rapidly-released mediators such as leukotriene and PAF (platelet activating factor) can be examined.

For example in the case of arachidonic acid-induced mouse ear edema a 28% inhibition of the edema is achieved with a dose of azelastine of 3 mg peroral/kg body weight mouse and a 41% inhibition with topical application of a dose of azelastine of 0.25 mg/kg mouse ear. In the case of rat paw edema (induced by carrageenin, determination of paw volume after one hour) a peroral dose of for example 3.9 mg/kg rat inhibited edema formation by 50%. The minimum effective dose in the above mentioned animal experiments is for example 1–2 mg/kg orally or 10 mg/kg with topical use (10 mg/kg correspond to about 0.25 mg/cm$^2$ body surface.

The general dose range to produce an effect (animal experiments as above) may for example be:

0.1–9 mg/kg orally, in particular 0.5–5 mg/kg;
2.5–80 mg/kg topically, in particular 5–40 mg/kg.

The anti-inflammatory effect of azelastine is, for example, comparable to the effect of the known pharmaceutically active ingredient indomethacin, but the following differences exist; no gastro-intestinal side effects such as gastric erosions, gastric ulcer or gastritis (indeed, azelastine even has a gastric mucosa-protecting effect), inhibition of leukotriene-synthesis (non-steroidal anti-inflammatory agents, such as indomethacin, promotes this), no influence on the synthesis of prostanoids (the well-known non-steroidal anti-inflammatory agents have an inhibitory effect in this case). Indications for this anti-inflammatory effect that may, for example, be considered are: inflammatory and degenerative forms of rheumatism, rheumatoid arthritis, gastritis, gastric and intestinal ulcers).

Azelastine also inhibits the ulcerous intestinal inflammation in the rat triggered by indomethacin (P. Del Soldato et al., Agents and Actions, Volume 16, 5, Publishers: Birkhäuser, Basel 1985, pages 393-396). Azelastine inhibits the formation of these intestinal lesions in a dose range of 8-80 mg/kg in a dose-dependent manner. This model demonstrates in particular the effect in *Colitis ulcerosa*. For example in the above mentioned experimental method with 5 peroral administrations of, in each case, 50 mg/kg body weight of rat (scheme of application after Del Soldato) inhibition of the inflammation of around 50% is achieved.

The minimum effective oral dose of azelastine in the above mentioned animal experiment is, for example, 16 mg/kg.

The general dosage range for this intestinal anti-inflammatory action (animal experiment as above) may, for example, be:

4-80 mg/kg orally, in particular 16-60 mg/kg.

This effect of azelastine is comparable with the effect of the known pharmaceutically active substance sulphasalazine, although it displays the following differences from that substance: lower dosage, broader pharmacological profile of action (inhibition of leukotriene synthesis and of formation of radicals). In view of this effect the following indications may, for example, be considered for azelastine:

*Colitis ulcerosa*, Morbus Crohn, inflammatory intestinal disorders (inflammatory bowel disease).

The individual dose of azelastine for use in *Colitis ulcerosa* and related disorders (for example Morbus Crohn, gastritis, rheumatoid arthritis, inflammatory and degenerative forms of rheumatism) may, for example, lie:

a) in oral medicinal forms between 2 and 24 mg, preferably 4 and 16 mg, in particular 4 and 8 mg;
b) in medicinal forms for local application on the skin and mucous membranes (for example in the form of solutions, lotions, emulsions, ointments, enemas and the like) between 0.1 and 10% by weight, preferably 0.7-5% by weight, in particular 1-5% by weight;
c) in the case of suppositories between 4 and 100 mg; preferably 6 and 80 mg, in particular 10 and 50 mg;
d) in the case of parenteral medicinal forms (for example injections, infusions and the like) between 0.1 and 30 mg, preferably 0.5 and 10 mg, in particular 1 and 5 mg.

(The doses are in each case related to the free base)

The individual dose of azelastine for use in gastric and intestinal ulcers may, for example, lie:

a) in the case of oral medicinal forms between 2 and 24 mg, preferably 4 and 16 mg, in particular 4 and 8 mg;
b) in the case of parenteral medicinal forms between 0.1 and 30 mg, preferably 0.5 and 10 mg, in particular 1 and 5 mg.

For example 1 to 2 tablets containing 4 to 8 mg of azelastine may be recommended 3 times daily. In the case of oral administration, the minimum daily dose is, for example, 4 mg; the maximum daily dose with oral administration should not exceed 24 mg.

In addition, azelastine also has a dose-related cytoprotective effect. It has been shown in rats that azelastine inhibits the ethanol-induced formation of mucous membrane damage in the stomach both after systemic and after oral administration and is thus, for example, indicated in gastritis and gastroduodenal ulceration.

The effect is, for example, tested in rats in which mucous membrane damage has been provoked in the stomach through administration of ethanol (Szelenyi and Brune, Dig. Dis. Sci., 33 (1988) page 865-871). Azelastine was administered orally (intragastrally) one hour before administration of the ethanol using an esophageal tube. Azelastine inhibited damage to the gastric mucosa in a dose range of 8-80 mg/kg to a dose-related extent.

The gastric mucosa-protecting effect of azelastine may be compared with that of known pharmaceutically active substances such as aluminium-containing antacids [$Al(OH_3)$] or sucralfate, although it displays the following differences: lower dose and more favorable pharmacological profile. Azelastine inhibits leukotriene synthesis, but does not influence prostaglandin synthesis. In addition azelastine also inhibits the formation of radicals.

Pharmaceutical formulations for use in the above mentioned indications generally contain between 2 and 16, preferably 4 to 8 mg of azelastine.

Administration in inflammatory disorders may, for example, be in the form of tablets, capsules, pills, coated tablets, suppositories, enemas, ointments, clysmas, jellys, gels, creams, powders, dusting powders, suspensions (aerosols) or in liquid form. Liquid forms which may, for example, be considered are: oils or alcoholic or aqueous solutions as well as suspensions and emulsions. Preferred forms of application are tablets containing between 2 and 16 mg preferably between 4 and 10 mg of azelastine. One to 2 tablets containing 4 to 8 mg of azelastine may, for example, be recommended 3 times daily. In the case of oral administration the minimum daily dose is, for example, 4 mg; the maximum daily dose in oral administration should not exceed 24 mg.

In the case of *Colitis ulcerosa* the use of capsules or sachets containing azelastine in the form of sustained release pellets having a release time for the active substance of 6 to 48 hours, preferably 12 to 24 hours, is particularly preferred.

The acute toxicity of azelastine in mouse (expressed as the LD 50 mg/kg; Method after Miller and Tainter: Proc. Soc. Exper. Biol. a. Med. 57 (1944) 261) is, for example, between 120 and 170 mg/kg in the case of oral application. (The doses are in each case related to the free base)

The pharmaceutical compositions or medicaments contain azelastine or its physiologically acceptable salts as active substance. The active substance is optionally present in a mixture with other pharmacologically or pharmaceutically active substances. The preparation of the medicaments is effected in conventional manner, it also being possible to use conventional and customary pharmaceutical auxiliary substances and other conventional carriers and diluents.

Carrier and auxiliary substances that may, for example, be considered are those which are recommended or quoted in the following literature references as auxiliary substances for pharmacy, cosmetics and related fields: "Ullmanns Encyklopädie der technischen Chemie", Volume 4 (1953), pages 1 to 39; Journal of Pharmaceutical Sciences, Volume 52 (1963), page 918 et seq.;

H.v.Czetsch-Lindenwald, "Hilfsstoffe fr Pharmazie und angrenzende Gebiete"; Pharm. Ind. issue 2 (1961), page 72 et seq.; Dr. H.P. Fiedler, "Lexikon der Hilfsstoffe fr Pharmazie, Kosmetik und angrenzende Gebiete" Cantor KG, Aulendorf in Wurttemberg 1981.

Examples of such additives are gelatin, natural sugars such as unrefined sugar or lactose, lecithin, pectin, starches (for example corn starch), cyclodextrines and cyclodextrine derivatives, polyvinyl pyrrolidone, polyvinyl acetate, gelatin, gum arabic, alginic acid, tylose, talcum, lycopodium, silica gel (for example colloidal), cellulose, cellulose derivatives (for example cellulose ether in which the cellulose hydroxy groups are partially etherified with lower saturated aliphatic alcohols and/or lower saturated aliphatic oxyalcohols, for example, methyloxypropyl cellulose, methyl cellulose, hydroxypropylmethyl cellulose, hydroxypropylmethyl cellulose phthalate); fatty acids as well as magnesium, calcium or aluminium salts of fatty acids with 12 to 22 carbon atoms, in particular saturated ones (for example stearates), emulsifiers, oils and fats, in particular vegetable fats (for example peanut oil, castor oil, olive oil, sesame oil, cottonseed oil, corn oil, wheat germ oil, sunflower seed oil, cod liver oil, in each case also hydrogenated; mono-, di- and triglycerides of saturated fatty acids $C_{12}H_{24}O_2$ to $C_{18}H_{36}O_2$ and their mixtures, pharmaceutically acceptable single or multivalent alcohols and polyglycols such as polyethylene glycols as well as derivatives thereof, esters of aliphatic saturated or unsaturated fatty acids (2 to 22 carbon atoms, in particular 10-18 carbon atoms) with monovalent aliphatic alcohols (1 to 20 carbon atoms), or polyhydroxy alcohols such as glycols, glycerin, diethylene glycol, pentaerythritol, sorbitol, mannitol, etc., which may optionally also be etherified, esters of citric acid with primary alcohols, acetic acid, benzylbenzoate, dioxolanes, glycerin formals, tetrahydrofurfuryl alcohol, polyglycol ether with $C_1$-$C_{12}$-alcohols, dimethylacetamide, lactamides, lactates, ethyl carbonates, silicones (in particular medium-viscous polydimethylsiloxanes), calcium carbonate, sodium carbonate, calcium phosphate, sodium phosphate, magnesium carbonate and the like.

Other auxiliary substances that may be used are substances which aid disintegration (so called disintegrants) such as: cross-linked polyvinyl pyrrolidone, sodium carboxymethyl starch, sodium carboxymethyl cellulose or microcrystalline cellulose. Known coating substances may also be used. Those that may, for example, be considered are: polymerizates as well as copolymerizates of acrylic acid and/or methacrylic acid and/or their esters; copolymerizates of acrylic and methacrylic acid esters with a low ammonium group content (such as Eudragit ® RS), copolymerizates of acrylic and methacrylic acid esters and trimethyl ammonium methacrylate (for example Eudragit ® RL); polyvinylacetate; fats, oils, waxes, fatty alcohols; hydroxypropyl methyl cellulose phthalate or acetate succinate; cellulose-, starch- as well as polyvinylacetate phthalate; carboxymethyl cellulose; methylcellulose phthalate, -succinate, -phthalate succinate and - phthalate-acid half esters; zein; ethyl cellulose as well as -succinate; shellac, gluten; ethylcarboxyethyl cellulose; ethacrylate-maleic acid anhydride copolymer; maleic acid anhydride-vinylmethyl ether copolymer; styrol-maleic acid copolymerizates; 2-ethyl-hexyl-acrylate maleic acid anhydride; crotonic acid-vinyl acetate copolymer; glutamic acid/glutaminic acid ester-copolymer; carboxymethylethyl-cellulose glycerin monooctanoate; cellulose acetate succinate; polyarginine.

Plasticizing agents for coating substances that may be considered are:

Citric and tartaric acid esters (acetyltriethyl-, acetyltributyl-, tributyl-, triethylcitrate); glycerin and glycerin esters (glycerin diacetate, -triacetate, acetylated monoglycerides, castor oil); phthalic acid esters (dibutyl-, diamyl-, diethyl-, dimethyl-, dipropyl-phthalate), D-(2-methoxy- or ethoxyethyl)-phthalate, ethylphthalyl-, butylphthalylethyl- and butylglycolate; alcohols (propylene glycol, polyethylene glycol of various chain lengths), adipates (diethyladipate), di-(2-methoxy- or ethoxyethyladipate); benzophenone; diethyl- and dibutylsebacate, -succinate, -tartrate; diethylene glycol diproprionate; ethylene glycol-diacetate, -dibutyrate, -dipropionate; tributylphosphate, tributyrin; polyethyleneglycol sobitan monooleate (polysorbates such as polysorbate 80); sorbitan monooleate.

For the manufacture of solutions or suspensions it is, for example, possible to use water or pharmaceutically acceptable organic solvents, such as, for example, ethanol, propanol, isopropanol, 1,2-propylene glycol, polyglycols and their derivatives, dimethylsulfoxide, fatty alcohols, triglycerides, partial esters of glycerins, paraffins and the like.

For injectable solutions or suspensions, it is, for example, possible to use non-toxic parenterally acceptable diluents or solvents, such as for example: water, 1,3-butanediol, ethanol, 1,2-propylene glycol, polyglycols in mixture with water, Ringer's solution, isotonic salt solution or also solidified oils including synthetic mono- or diglycerides or fatty acids such as oleic acid.

In the manufacture of the formulations it is, for example, possible to use known and conventional solubilizers or emulsifiers. Solubilizers and emulsifiers which may, for example, be used are: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters or sorbitan, polyoxyethylated fats, polyoxyethylated oleotriglycerides, linolizated oleotriglycerides, polyethyleneoxide condensation products of fatty alcohols, alkylphenols or fatty acids or also 1-methyl-3-(2-hydroxyethyl)-imidazolidone-(2). In this case polyoxyethylated means that the substances in question contain polyoxyethylene chains, the degree of polymerization of which generally lies between 2 and 40 and in particular between 10 and 20.

Polyoxyethylated substances of this kind may, for example, be obtained through reaction of hydroxyl group-containing compounds (for example mono- or diglycerides or unsaturated compounds such as those containing oleic acid residues) with ethylene oxide (for example 40 mol ethylene oxide per mol glyceride).

Examples of oleotriglycerides are olive oil, peanut oil, castor oil, sesame oil, cottonseed oil, corn oil. See also Dr. H.P. Fiedler "Lexikon der Hilfsstoffe fr Pharmazie, Kosmetik und angrenzende Gebiete" 1971, pages 191-195.

In addition, it is also possible to add preservatives, stabilizers, buffer substances, for example, calcium hydrogen phosphate, colloidal aluminium hydroxide, flavor correcting substances, sweeteners, colorants, antioxidants and complex formers, for example, ethylene diamino-tetra-acetic acid) and the like. Adjustment to a pH range of ca. 3 to 7 is optionally possible using pharmaceutically acceptable acids or buffers to stabilize the molecule of active substance. In general a neutral to weakly acidic (up to pH 5) pH value is preferred.

For the preparation of dermally applied formulations it is possible to use the above mentioned substances and spreadable or liquid hydrocarbons such as Vaseline or paraffin or gels of paraffin hydrocarbons and polyethylene, fats and oils of plant or animal origin which may in part also be hydrated or synthetic fats such as glycerides of the $C_8-C_{18}$ fatty acids, as well as beeswax, cetylpalmitate, wool wax, wool wax alcohols; fatty alcohols such as cetyl alcohol, stearyl alcohol, polyethylene glycols of molecular weight 200 to 20,000; liquid waxes such as isopropylmyristate, isopropylstearate, ethyloleate; emulsifiers such as sodium, potassium and ammonium salts of the stearic acids or palmitic acids as well as triethenolamine stearate, alkali salts of the oleic acids, ricinic acid, salts of sulfurated fatty alcohols such as sodium lauryl sulphate, sodium acetyl sulphate, sodium stearyl sulphate, salts of gallic acid, sterols such as cholesterol, partial fatty acid esters of multivalent alcohols such as ethylene glycol monostearate, glycerol monostearate, pentaerythritol monostearate, partial fatty acid esters of sorbitan, partial fatty acid esters of polyoxyethylene sorbitan, sorbitol ethers of polyoxyethylene, fatty acid esters of polyoxyethylene, fatty alcohol ethers of polyoxyethylene, fatty acid esters of saccharose, fatty acid esters of polyglycerol, lecithin.

Antioxidants that may, for example, be considered are sodium metabisulfite, ascorbic acid, gallic acid, gallic acid alkyl ester, butylhydroxyanisole, nordihydroguaiaretic acid, tocopherols as well as tocopherols+-synergists (substances which bind heavy metals through complex formation, for example, lecithin, ascorbic acid, phosphoric acid). The addition of synergists substantially enhances the anti-oxygenic effect of the tocopherols.

The preservatives that may, for example, be considered are sorbic acid, p-hydroxybenzoic acid esters (for example lower alkyl esters), benzoic acid, sodium benzoate, trichloroisobutylalcohol, phenol, cresol, benzethonium chloride and formalin derivatives.

The pharmaceutical and galenic treatment of the compounds of the invention is effected according to the conventional standard methods. For example, active substance(s) and auxiliary and/or carrier substances are well mixed by means of stirring or homogenizing (for example using conventional mixing devices), working generally taking place at temperatures between 20° and 80° C., preferably 20° to 50° C., particularly at room temperature. In this connection reference is also made to the following standard work: Sucker, Fuchs, Speiser, "Pharmazeutische Technologie", publishers: Thieme-Verlag Stuttgart, 1978.

Application may be to the skin or mucous membrane or to the inside of the body, for example, oral, enteral, pulmonal, rectal, nasal, vaginal, lingual, intravenous, intraarterial, intracardial, intramuscular, intraperitoneal, intracutaneous or subcutaneous. The parenteral forms of preparation are in particular sterile or sterilized preparations.

For the treatment of psoriasis, azelastine is used locally, for example, in the form of solutions, tinctures, suspensions, emulsions, ointments, gels, creams, pastes, lotions or shampoos. Anhydrous formulations are preferably used, facilitating thereby the concomitant use of salicylic acid and/or urea. Formulations of this type, which may also be made washable through the addition of surfactants, are, for example, described in German published patent 36 03 859. The urea may either be present as a surfactant-urea compound or also in free form. Formulations containing neither urea nor salicylic area may of course also be used.

The concentrations of azelastine used in this case may, for example, be 0.1 to 10% (weight/weight), preferably 0.5 to 8%, in particular 1 to 5%. The concentrations of salicylic acid are, for example, 0.1 to 10%, preferably 0.2 to 8%, in particular 0.5 to 5%. The concentrations of urea used are, for example, 1 to 20%, preferably 3 to 18%, in particular 5 to 15%.

For topical application, and also for formulation as a medicine for other forms of application, it has, for example, been found advantageous to use azelastine together with at least one alkyl glycerin with 2 to 12 carbon atoms in the alkyl radical, which may be present in the form of an ether group bound to one of the primary or secondary OH groups of the glycerin. Alkyl glycerins of this type boost or improve the effect of azelastine. Alkyl glycerins with 3 to 9 carbon atoms are preferably used here, alone or in a mixture.

Particularly favorable effects are therefore displayed by a pharmaceutical composition which
  a) contains azelastine and
  b) an alkyl glycerin of the general formula I

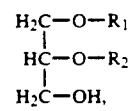

in which one of the radicals $R_1$ and $R_2$ represents an alkyl group with 2 to 12 carbon atoms and the other radical represents a hydrogen atom,
  as well as optionally other conventional pharmacological additives and diluents.

Preferably there is used a mixture of (a) water and (b) a mixture of alkyl glycerins which contains nonyl or octyl glycerin, hexyl or pentyl glycerin and propyl or ethyl glycerin. A corresponding formulation for topical use contains, for example, 1 to 100 mg of azelastine per ml of alkyl glycerin of Formula I or a corresponding alkyl glycerin mixture with water.

A mixture of this type is hereinafter also referred to as a cascade.

The amount of azelastine in mg/ml of cascade is designated by an index shown hereafter, in such a manner that, for example, a cascade mixture containing 40 mg/ml of azelastine is termed a Cascade 40 and a mixture with 60 mg of azelastine per ml of cascade is termed a Cascade 60.

The manufacture of the alkyl glycerins is known, for example, from Published German Patent Specification DE-OS 33 43 530.8. Preference is, for example, given to alkyl glycerin-water mixtures which contain, for example, nonyl glycerin, octyl glycerin, hexyl glycerin, pentyl glycerin, propyl glycerin and ethyl glycerin. Aqueous mixtures of this kind contain, for example, three of the glycerin ethers mentioned, namely a lower (ethyl, propyl), a middle (pentyl, hexyl) and a higher one (octyl, nonyl) in which the amount by weight of the lower ether is about as large as the sum of the amounts by weight of the two other glycerin ethers. The amount of water is about equal to the amount of the lower glycerin ether and is, for example, half the total amount of the glycerin ethers present. Examples of glycerin ether-water mixtures of this type are listed below:

|  | Water | Glycerin propylether | Glycerin hexylether | Glycerin- nonyl ether |
|---|---|---|---|---|
| Parts by wt. | 2 | 2 | 1 | 1 |

|  | Water | Glycerin ethylether | Glycerin pentylether | Glycerin- octyl ether |
|---|---|---|---|---|
| Parts by wt. | 2 | 2 | 1 | 1 |

Pharmaceutical compositions containing alkyl glycerins of Formula I are particularly suitable for topical application. In order to treat, for example, psoriasis and related disorders, Cascade 1 to Cascade 100 is, for example, rubbed into the skin areas affected two to three times daily. No harmful side effects have been observed to date.

Topical treatments with an azelastine-cascade mixture can, however, also be applied in the treatment of, for example, internal inflammatory disorders through rubbing into a large area of the skin. Resorption through the skin then leads to therapeutically effective blood levels. An advantage of this form of application lies in the fact that the cascade formulations are tolerated by the skin without difficulty.

Presentation of the azelastine in the form of a cascade formulation (for example in the form of the solutions Cascade 1 to Cascade 100) is also suitable for the manufacture of suppositories for rectal insertion. This is also an effective method of treating internal inflammatory disorders.

A particularly favorable carrier mixture for azelastine consists of a mixture of about 4 parts by weight of water, 4 parts by weight propyl glycerin and 2 parts by weight each of hexyl glycerin and non-glycerin.

To manufacture pharmaceutical compositions containing azelastine in the presence of a glycerin ether of Formula I or of a mixture of glycerin ethers of this type of Formula I, the azelastine is, for example, used with 10000 to 0.05, for example 1000 to 5 or 700 to 7, preferably 30 to 10 parts by weight (related in each case to one part by weight of azelastine) of at least one glycerin ether of Formula I or a mixture of such glycerin ethers as well as optionally 10000 to 0.05, for example 400 to 2, preferably 20 to 3 parts by weight of water (also related to one part by weight of azelastine). This mixture with the glycerin ethers can be effected at the beginning of the manufacture of the corresponding pharmaceutical composition, but optionally also during a later stage in manufacture.

DETAILED DESCRIPTION OF PREFERRED EMBODIMENTS

The following examples illustrate the invention.

1. Example of a formulation for the topical treatment of psoriasis

This example relates to a solution of 8.8% of azelastine hydrochloride in a mixture of solvents referred to as Cascade 0 (azelastine 8%).

Preparation of the Cascade 0

1000 g of water, 1000 g of glycerin-1-n-propyl ether, 500 g of glycerin-1-n-hexyl ether and 500 g of glycerin-1-n-nonyl ether are mixed in a suitable vessel.

Preparation of the azelastine solution

About 2.5 liters of Cascade 0 are measured into a suitable vessel and 264 g of azelastine hydrochloride dissolved in this mixture of solvents. The resulting solution is then made up to 3 liters with Cascade 0.

The density of the solution of 1.023 g/ml at 22° C. This solution is sterile filtered under aseptic conditions into a sterile vessel through a membrane filter having a pore size of 0.2 µm and filled in sterile dropper bottles of 10 ml each. Each ml of solution contains mg of azelastine (corresponding to 88 mg of azelastine-HCl).

2. Azelastine film-coated tablets for oral application

Preparation of the tablets

A premix is prepared of 440 g of azelastine-HCl, 360 mg of micro crystalline cellulose and 200 g of talcum. This premix together with 6000 g of lactose monohydrate, 2870 g of microcrystalline cellulose and 100 g of highly disperse silicon dioxide are passed through a sieve and homogenized in a sutable mixer. 30 g of magnesium stearate are sieved into the mixture so obtained and the resulting mixture is homogenized one more time. The mass so obtained is pressed into tablets weighing 100 mg having a diameter of 6 mm and a radius of curvature of 5.5 mm.

Preparation of the film-coated tablets

The tablets are continuously sprayed in a vessel suitable for this purpose with 1.2 kg of a film suspension.

The film suspension is prepared by dissolving 60 g of polyethylene glycol 6000, 12 g of polysorbate 80 and 9.6 g of carboxymethyl cellulose sodium in 787.2 g of water. 120 g of talcum, 120 g of titanium dioxide and 1.2 g of simethicone[1] are dispersed in this solution and then 90 g of a copolymerizate based on dimethylaminoethyl methacrylate and neutral methacrylic acid esters added with gentle stirring in the form of a 30% aqueous dispersion (Eudragit ® E 30 D).

[1] Simethicone is a mixture of polydimethyl siloxane (predominantly 90-99% by weight) and silicon dioxide (for example 4-7% by weight); U.S. Pharmacopoeia, 21st edition Each film tablet contains 4 mg of azelastine (corresponding to 4.4 mg of azelastine hydrochloride).

3. Azelastine 8 mg film-coated tablets

Preparation of film-coated tablets for the treatment of *Colitis ulcerosa*

88 g of azelastine hydrochloride, 701 g of lactose monohydrate and 701 g of microcrystalline cellulose are sieved, mixed and moistened with 1440 g of a ph-independent acrylic resin lacquer substance which forms poorly permeable coatings (Eudragit ® RS 12.5). The moist mass is granulated through a sieve and dried.

The dry granulate, 100 g of talcum and 30 g of magnesium stearate are sieved again and homogenized in a suitable mixture. This mass is pressed into tablets weighing 180 mg having a diameter of 8 mm and a radius of curvature of 6 mm.

To prepare the film-coated tablets the tablets are sprayed in an apparatus conventionally used for this purpose with a film suspension manufactured as follows. 18 g of magnesium stearate are dispersed in 664 g of isopropanol with stirring; 18 g of 1,2 propylene glycol and 800 g of Eudragit ® S 12.5 (an anionic polymerizate of methacrylic acid and methacrylic acid esters that contains a softener, is gastric juice resistant and only soluble beyond pH 7) are then worked into this suspension.

Each film-coated tablet contains 8 mg of azelastine (corresponding to 8.8 mg of azelastine hydrochloride).

4. Azelastine 8 mg capsules (preferably for the treatment of *Colitis ulcerosa*)

100 g of azelastine hydrochloride, 200 g of tartaric acid, 500 of lactose and 700 g of microcrystalline cellulose are mixed and pasted with about 700 g of purified water. The moist mass is pressed through a perforated place having a hole diameter of 1 mm and the resultant strands divided and rounded in the conventional manner by treatment on a spheronizer disc. The pellets obtained are dried and sieved.

1000 g of pellets of the sieve fraction 800 to 1200 μm are sprayed with a suspension that is prepared as follows:

0.6 g of polysorbate 80 are dissolved in 190 g of purified water and 40 g of triethyl citrate are emulsified into the solution. 800 g of Eudragit ® RS 30 D (a 30% aqueous dispersion of a copolymerizate of acrylic and methacrylic acid esters having a low content of trimethyl ammonium methacrylate chloride) are added to the emulsion thereby obtained and stirred for about 10 minutes.

109.2 g of talcum and 0.2 g of silicone anti-foaming oil (Simethicone) are suspended in 860 g of purified water. This suspension is stirred into the above obtained dispersion.

The lacquering suspension so obtained is applied to the pellets in the conventional manner, for example using a fluidized bed spray granulator at an inlet air temperature of 40°-50° C. and a maximum outlet air temperature of 40° C. The pellets are dried under the same conditions.

The lacquering suspension is sprayed onto the pellets until the total weight of the dried pellets is 1127 g.

The lacquered pellets are filled in batches of 148.7 mg into si 1 hard gelatin capsules. Each hard gelatin capsule contains 8.8 mg azelastine hydrochloride, corresponding to 8 mg of azelastine, in a sustained release formulation. The release of azelastine hydrochloride from this dosage form is tested according to the process given in the US Pharmacopoeia, 21st edition (USP XXI) using the Dissolution Test Apparatus 2. The release of azelastine hydrochloride 500 ml of test solution at 37° C. is determined at a paddle speed of 1 revolutions per minute. The test solution consists, for the first 2 hours, of 0.1 molar hydrochloric acid, after which the pellets are transferred to phosphate buffer solution of pH 6.8 of the European Pharmacopoeia. In each case the release of azelastine hydrochloride is measured from the test solutions. The release is after 1 hour 5.5% in 0.1 m HCl
after 2 hours 8.4% in 0.1 m HCl
after 3 hours 11.2% in phosphate buffer pH 6.8
after 4 hours 14.3% in phosphate buffer pH 6.8
after 5 hours 21.7% in phosphate buffer pH 6.8
after 6 hours 31.7% in phosphate buffer pH 6.8
after 7 hours 39.2% in phosphate buffer pH 6.8
after 8 hours 48.5% in phosphate buffer pH 6.8
after 9 hours 56.1% in phosphate buffer pH 6.8
after 10 hours 64.0% in phosphate buffer pH 6.8
after 11 hours 74.5% in phosphate buffer pH 6.8
after 12 hours 81.2% in phosphate buffer pH 6.8

What is claimed is:

1. A method for treating a psoriasis disorder which comprises topically or orally administering a pharmaceutically effective dose of a member of the group consisting of azelastine and its pharmaceutically acceptable salts.

2. A method as set forth in claim 1 in which the azelastine is administered in the form of a pharmaceutically effective composition comprising a member of the group consisting of azelastine and its pharmaceutically acceptable salts, as active ingredient, and a pharmaceutically acceptable carrier therefor.

3. A method according to claim 2 in which the carrier comprises an alkyl glycerin of the general formula I:

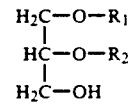

wherein one of the radicals $R_1$ and $R_2$ is an alkyl group with 2-12 caron atoms and the other of the radicals $R_1$ and $R_2$ represents a hydrogen atom.

4. A method according to claim 3 in which the pharmaceutically effective composition contains 10000 to 0.05 parts by weight of alkyl glycerin of formula I or a mixture of alkyl glycerin of formula I, in each case for each part by weight of azelastine.

5. A method according to claim 3 in which the pharmaceutically effective composition contains 10000 to 0.05 parts by weight of water for each part by weight of azelastine.

6. A method as set forth in claim 2 in which the pharmaceutically acceptable carrier is topically acceptable.

* * * * *